United States Patent
Sibue et al.

(10) Patent No.: US 12,064,392 B2
(45) Date of Patent: Aug. 20, 2024

(54) MODULE AND DEVICE FOR EMITTING ELECTROMAGNETIC WAVES

(71) Applicant: Remedee Labs, Saint Ismier (FR)

(72) Inventors: Pierre-Yves Sibue, Jarrie (FR); Jacques Husser, Saint Ismier (FR); Michael Foerster, Corenc (FR); David Crouzier, Meylan (FR)

(73) Assignee: REMEDEE LABS (FR)

( * ) Notice: Subject to any disclaimer, the term of this patent is extended or adjusted under 35 U.S.C. 154(b) by 1019 days.

(21) Appl. No.: 16/823,037

(22) Filed: Mar. 18, 2020

(65) Prior Publication Data

US 2020/0253822 A1    Aug. 13, 2020

Related U.S. Application Data

(63) Continuation-in-part of application No. PCT/EP2018/075232, filed on Sep. 18, 2018, and a
(Continued)

(30) Foreign Application Priority Data

Sep. 18, 2017 (FR) ...................................... 17/58633
Sep. 18, 2017 (FR) ...................................... 17/58634

(51) Int. Cl.
*A61H 39/00* (2006.01)
*A61N 1/08* (2006.01)
(Continued)

(52) U.S. Cl.
CPC ............... *A61H 39/00* (2013.01); *A61N 1/40* (2013.01); *A61H 2039/005* (2013.01);
(Continued)

(58) Field of Classification Search
CPC .............. A61H 39/00; A61H 2039/005; A61H 2201/0157; A61H 2201/165;
(Continued)

(56) References Cited

U.S. PATENT DOCUMENTS 5,575,761 A * 11/1996 Hajianpour ........ A61H 23/0263
601/48
6,122,550 A     9/2000 Kozhemiakin et al.
(Continued)

FOREIGN PATENT DOCUMENTS

CN          101778650 A      7/2010
DE     102015109819 A1      12/2016
(Continued)

OTHER PUBLICATIONS

International Search Report and Written Opinion issued Nov. 23, 2018 in PCT Application No. PCT/EP2018/075232, and English translation of ISR.
(Continued)

*Primary Examiner* — Tu A Vo
*Assistant Examiner* — Kelsey E Baller
(74) *Attorney, Agent, or Firm* — Dilworth IP, LLC

(57) ABSTRACT

A portable device and method for transmitting electromagnetic waves. In one aspect, when arranged at a surface, the device is capable of transmitting waves having a power flux density of at least 0.5 milliwatts per square centimeter of surface area and a frequency value of between 3 and 120 gigahertz. The device is further capable of simultaneously exposing at least 2.5 square centimeters of the surface to the waves.

16 Claims, 9 Drawing Sheets

Related U.S. Application Data continuation-in-part of application No. PCT/EP2018/075236, filed on Sep. 18, 2018.

(51) Int. Cl.
*A61N 1/40* (2006.01)
*A61N 5/02* (2006.01)

(52) U.S. Cl.
CPC ........... *A61H 2201/0157* (2013.01); *A61H 2201/165* (2013.01); *A61H 2205/027* (2013.01); *A61H 2205/065* (2013.01); *A61H 2205/081* (2013.01); *A61H 2205/106* (2013.01); *A61N 2001/083* (2013.01); *A61N 5/02* (2013.01)

(58) Field of Classification Search
CPC ...... A61H 2201/501; A61H 2201/5025; A61H 2201/5097; A61H 2205/027; A61H 2205/065; A61H 2205/081; A61H 2205/106; A61H 2230/655; A61N 1/40; A61N 5/02; A61N 5/022; A61N 5/04; A61N 2001/08
See application file for complete search history.

(56) References Cited

U.S. PATENT DOCUMENTS

| | | | | |
|---|---|---|---|---|
| 6,596,016 | B1* | 7/2003 | Vreman | A61N 5/0621 |
| | | | | 128/903 |
| 9,731,126 | B2* | 8/2017 | Ferree | A61B 5/11 |
| 10,279,179 | B2* | 5/2019 | Gozani | A61B 5/4809 |
| 2006/0167531 | A1 | 7/2006 | Gertner et al. | |
| 2008/0058783 | A1* | 3/2008 | Altshuler | A61N 5/0616 |
| | | | | 606/9 |
| 2010/0036369 | A1 | 2/2010 | Hancock | |
| 2015/0082406 | A1* | 3/2015 | Park | H04L 63/105 |
| | | | | 726/9 |
| 2016/0034679 | A1* | 2/2016 | Yun | G06V 40/10 |
| | | | | 340/5.83 |
| 2016/0235980 | A1* | 8/2016 | Berman | A61B 5/377 |
| 2017/0056238 | A1* | 3/2017 | Yi | A61F 7/007 |
| 2017/0209708 | A1* | 7/2017 | Schwarz | A61N 2/004 |
| 2019/0110950 | A1* | 4/2019 | Smith | G06F 1/163 |
| 2021/0330547 | A1* | 10/2021 | Moaddeb | A61N 1/0456 |

FOREIGN PATENT DOCUMENTS

| | | |
|---|---|---|
| JP | 2009148492 A | 7/2009 |
| WO | 2012/022538 A1 | 2/2012 |
| WO | 2012022538 A1 | 2/2012 |
| WO | WO-2020175714 A1 * | 9/2020 |

OTHER PUBLICATIONS

International Search Report and Written Opinion issued Nov. 26, 2018 in PCT Application No. PCT/EP2018/075236, and English translation of ISR.

European Office Action issued Feb. 3, 2021, in connection with EP Application No. 18768909.6, and machine translation thereof.

European Office Action issued Feb. 3, 2021, in connection with EP Application No. 18766299.4, and machine translation thereof.

Notice of Reasons for Rejection issued Oct. 24, 2022 in connection with Japanese Patent Application No. 2020-537051 with machine translation.

Notice of Reasons for Rejection issued Oct. 24, 2022 in connection with Japanese Patent Application No. 2020-537050 with machine translation.

Chinese Office Action issued Jun. 22, 2022 in connection with Chinese Patent Application for Invention No. 201880067953.6, with English text translation.

Certified an Extract regarding European Patent Application No. 18768909.6 with PCT Form IB/304.

Certified an Extract regarding European Patent Application No. 18766299.4 with PCT Form IB/304.

Decision of Rejection issued Dec. 28, 2022 in connection with Chinese Patent Application No. 201880067953.6 with machine translation.

Notification under Rule 94(3) EPC issued Nov. 15, 2022 in connection with European Patent Application No. 18768909.6.

Notification under Rule 94(3) EPC issued Nov. 15, 2022 in connection with European Patent Application No. 18766299.4.

Radzievsky, A.A. et al., Electromagnetic MillimeterWave Induced Hypoalgesia: Frequency Dependence and Involvement of Endogenous Opioids, Bioelectormagnetics, 2008, pp. 284-295.

* cited by examiner

MODULE AND DEVICE FOR EMITTING ELECTROMAGNETIC WAVES

RELATED APPLICATIONS

The present application is a Continuation-in-Part under 35 U.S.C. § 111, and claims the benefit of and priority to, International Patent Application No. PCT/EP2018/075232 filed on Sep. 18, 2018, which in turn claims priority to French Patent Application No. 17/58634, filed Sep. 18, 2017. The present application is also a Continuation-in-Part under 35 U.S.C. § 111, and claims the benefit of and priority to, International Patent Application No. PCT/EP2018/075236, filed on Sep. 18, 2018, which in turn claims priority to French Patent Application No. 17/58633, filed Sep. 18, 2017. All of the foregoing applications are hereby incorporated by reference in their entirety for all purposes.

BACKGROUND

The invention relates to the treatment of pain, in particular the treatment of chronic pain of low to moderate intensity.

A significant part of the population suffers from chronic pain. By definition, chronic pain is recurrent, or even continuous, and can occur for months or years, without the origin being necessarily determined or eliminated. In the absence of a way to neutralize the source, it is therefore necessary to relieve the patient by reducing, or even eradicating, the symptom, that is to say, the pain.

Currently, the most common approach to treating a patient's pain, such as chronic pain, is to administer so-called analgesic drugs, especially when the pain occurs, to calm it down. These analgesic drugs may contain paracetamol, opiate derivatives, such as codeine or morphine, anti-inflammatory drugs, such as ibuprofen, or anesthetics.

However, regular intake of such analgesic active ingredients can cause undesirable side effects (for example: nausea, drowsiness, heartburn).

An alternative to taking medication is to treat the pain by physical methods. The risk of side effects is then reduced, as well as that of drug dependence.

There is, in particular, a known form of treatment by transcutaneous electrical neurostimulation (or TENS for "Transcutaneous electrical nerve stimulation") which consists in circulating an electric current in an area of the patient's body to stimulate nerves in order to reduce pain. However, the use of this technique requires a bulky device composed of electrodes to be placed on the patient's body and connected to an electric generator. In addition, it produces a tingling feeling which can be experienced as unpleasant by the patient.

There are also known forms of treatment called "alternative medicine" such as acupuncture, reflexology or even Chinese medicine. Although the effectiveness of some of these practices has been demonstrated, there is no clearly established scientific basis to support their modus operandi.

Lastly, it is a known fact that therapy by transmission of so-called "millimeter" waves (that is to say, whose frequency is less than 300 gigahertz reduces pain (see the publication by Usichenko TI, Edinger H, Gizkho V V, Lehmann C, Wendt M, Feyerherd F: "Low-intensity electromagnetic millimeter waves for pain therapy. Evid Based Complement Alternat Med"). Indeed, it was shown that the exposure of an area of the human body to millimeter electromagnetic waves allowed the release of endogenous opioids (see the publication by Rojavin M A, Ziskin M C: "Electromagnetic millimeter waves increase the duration of anaesthesia caused by ketamine and chloral hydrate in mice Int J Radiat Biol"), generating in the brain the synthesis of enkephalin, a natural peptide involved in pain tolerance.

Therefore, this technique makes it possible to avoid the disadvantages of therapies with analgesics or by neurostimulation, and its modus operandi is understood. In addition, transmitting millimeter waves can also be used in the treatment of anxiety or sleep disorders.

Application WO2012/022538, based on this principle, discloses a device aimed at reducing pain in a patient by transmitting electromagnetic waves to the surface of the patient's body. The device is bulky and has an imposing horn shape which requires that the patient be brought to a specific location holding the device, or that the device be transported to the patient, who cannot therefore keep it on him and use it at any time and place. In addition, the patient must preferably be assisted by one or more persons, specially trained to operate the device. The significant volume of the device is largely due to the wave transmitting elements, such as the generator and the antenna(s), which must provide, in order for the treatment to be effective, frequency waves between 30 and 300 GHz, which must have a high power flux density.

The CEM Tech Company markets a less bulky device aimed at reducing pain by means of electromagnetic waves. Although this device is small, the level of power flux density of the transmitted waves is from $10^{-19}$ to $10^{-5}$ watts/cm$^2$. Now, it is known that the analgesic effect of millimeter waves is not observed for a power flux density of less than 0.5 mW/cm$^2$ (see the publication by Rojavin M A, Radzievsky A A, Cowan A, Ziskin M C: "Pain relief caused by millimeter waves in mice: results of cold water tail flick tests".).

SUMMARY OF THE INVENTION

Therefore, an object of the invention is to treat pain effectively by means of electromagnetic waves, and to make the devices provided for this purpose accessible and easily usable by patients. Another object of the invention is to use this device for other purposes, such as the generation of a feeling of well-being, the treatment of anxiety or even sleep disorders.

To this end, the invention provides a portable device for transmitting electromagnetic waves capable, when it is affixed at a surface, of transmitting waves having a power flux density of at least 0.5 milliwatts per square centimeter of surface and a frequency value of between 3 and 120 gigahertz, the device being further capable of simultaneously exposing at least 2.5 square centimeters of the surface to the waves.

Thus, the device is portable, that is to say, capable and intended to be worn by a patient on a regular basis, or even continuously, without significant effort and without logistical or practical disadvantages. In addition, the power flux density of at least 0.5 milliwatts per square centimeter of surface allows the treatment to be effective and to reduce pain. Finally, the frequency is a frequency band particularly effective for the treatment by millimeter waves. Moreover, the study by Radzievsky A A, Gordiienko O V, Alekseev S, Szabo I, Cowan A, Ziskin M C: "Electromagnetic millimeter waves for pain therapy Evid Based Complement Alternat Med" tends to show that the optimal effect of a treatment by millimeter waves is obtained with a frequency around 61.25 GHz and a power flux density of approximately 13 mW/cm$^2$.

Concerning the aptitude to expose at least 2.5 square centimeters of surface, the device may, for example, present a module comprising several antennas transmitting waves simultaneously, the area covered by all the antennas, and therefore by the module, representing at least 2.5 continuous square centimeters exposed to waves in a homogeneous way. This makes it possible to obtain a surface continuously exposed to waves in a manner sufficient to induce the expected biological response.

Alternatively, the module may be capable of discontinuously exposing 2.5 cm² to waves, that is to say, several surface portions distributed over several different locations which, all together, represent 2.5 cm² of simultaneously irradiated surface.

It should be noted that the frequency transmitted by the different antennas is not necessarily the same. The different antennas may transmit different frequencies, being supplied by different ASICs. Nevertheless, the frequencies remain within the band of interest.

Advantageously, the waves have a power flux density of between 5 and 35 mW/cm².

Thus, it is a particularly efficient power band. On the other hand, some standards do not allow a power density greater than 35 mW/cm², so that the device may be calibrated so as not to exceed this limit, if necessary.

Preferably, the surface being human or animal skin, the device comprises a unit for detecting human or animal skin, the device being capable of signaling the presence or absence of the skin to be exposed to waves, and preferably capable of determining a distance between the skin and the device.

"Exposing to the waves" also means "irradiating by the waves".

Thus, the device transmits waves directly to the subject's skin only if the skin is detected. If the skin is not detected, or if the distance between the device and the skin is too significant, no transmission takes place. This prevents sending waves in any direction and allows saving energy. It is also possible to adapt the power or other parameters of the waves transmitted based on the estimated distance between the device and the skin.

Advantageously, the device is able to be worn at least in one of the following sites:
around a wrist;
on a leg;
on an ankle;
in the back;
on an ear;
in the palm of a hand; or
more generally any site presenting a strongly innervated area.

Thus, it is affixed at one of these sites, for example, around the wrist, like a watch, so as to be worn without particular inconvenience for the patient. Concerning heavily innervated areas, the study "Radzievsky A A, Rojavin M A, Cowan A, Alekseev S I, Ziskin M C. Hypoalgesic effect of millimeter waves in mice: Dependence on the site of exposure. Life sciences. 2000; 66 (21): 2101-11" demonstrated the beneficial therapeutic effect of sending millimeter waves in such areas.

Preferably, the device comprises a rechargeable battery.

Thus, it works wirelessly. Alternatively, it may operate by wire, in order to deliver higher powers or over longer durations.

Preferably, the device comprises a heat sink comprising at least one of the following elements:
a flexible material;
a phase change material;
a thermal buffer;
graphite; and
an elastomeric material.

Thus, the heat sink makes it possible to minimize heating of the device in order to maintain it at a temperature below 43° C. If it is flexible, it allows it to adapt to the shape of the device and its maneuverability.

Advantageously, the device comprises a unit for determining at least one data from the surface, for example, an impedance data.

Thus, this is carried out after transmitting the electromagnetic waves, by measuring the output power which is based on the adaptation of relative impedance to the skin. The device thereby obtains automatically one or more characteristics of the patient's skin.

Preferably, the device comprises a processing unit making it possible to deduce from the or each determined data at least one wave transmission parameter.

Thus, the data obtained are autonomously processed by the device which itself adapts the parameters of the waves, without any intervention by the patient who only has to activate or program the wave transmission without worrying about settings and adapting the waves to his own body.

The invention also provides a module for transmitting electromagnetic waves, which has a total volume of less than 4 cubic centimeters, preferably less than 3 cubic centimeters, and is suitable, when it is arranged at a surface, to transmit electromagnetic waves having a power flux density of at least 0.5 milliwatts per square centimeter of surface.

Thus, this module is particularly miniaturized, which allows it to be integrated into portable devices or to transport and use it easily. The minimum power flux density of 0.5 mW/cm² is that from which millimeter wave treatment is effective for treating pain, but this module may be intended for other uses.

The invention also provides a method of transmitting electromagnetic waves, in which a transmitter worn by a human or animal subject transmits electromagnetic waves towards the subject's skin, said waves having a power flux density of at least 0.5 milliwatts per square centimeter of skin and a frequency between 3 and 120 gigahertz.

Advantageously, the method comprises the following steps:
a unit detects human or animal skin, and
when the unit detects that the skin is located at three millimeters or less from the transmitter, the transmitter transmits the waves.

Another predetermined distance may be considered. The distance of 3 mm corresponds to a distance close enough to allow the skin to absorb almost all of the power of the electromagnetic radiation, even if the module is not in contact with the skin, for example, when moving the device or if the latter is not affixed by being pressed against the patient's body.

Preferably, the method includes the following steps:
determining at least one impedance data of the skin; and
depending on the or each data, adapting at least one transmission parameter.

Preferably, the wave transmission takes place at at least one predetermined acupuncture point of the subject.

Indeed, several publications demonstrated a particularly analgesic effect of millimeter waves at acupuncture points, just as the Lyensuk V P, Samosyuk I Z, Kulikovich Y N, Kozhanova A K study: "Experimental study on the low-intensity millimeter-wave electro-magnetic stimulation of acupuncture points" did. Wearing the device on the wrist, in particular on the acupuncture point Pericardium 6, the wrist being an area particularly rich in nerve endings, makes it possible to increase the effectiveness of the millimeter wave treatment.

Advantageously, the transmission is controlled at the transmitter or by means of a device able to communicate with the transmitter through a telecommunication network.

The invention also provides a computer program comprising code instructions capable of controlling the implementation of the steps of the method described above when it is executed on a computer.

This computer program may be included in computer software but also in an application for a mobile terminal such as a smartphone or a "smartwatch", otherwise called "connected watch".

The invention also provides a method of accessing the program according to the invention for downloading onto a communication network.

Lastly, the invention provides a device comprising telecommunication means and the program according to the invention.

Thus, this device may be, for example, a computer or a smartphone.

According to another apsect, the invention provides a wave transmission module, which has a total volume of less than 4 cubic centimeters, preferably less than 3 cubic centimeters, and is capable, when it is placed on a surface, to transmit electromagnetic waves having a power surface density of at least 0.5 milliwatts per square centimeter of surface.

Thus, this module of small size may be integrated into an easily handled device, for example, portable, such as a smartphone or a smartwatch, or be integrated in large numbers into a more complex device generating high radiation without taking up a large space within the device. In addition, starting from 0.5 mW/cm$^2$, it is known that an effect in the treatment of pain is obtained (see the publication by Rojavin M A, Radzievsky A A, Cowan A, Ziskin M C: "*Pain relief caused by millimeter waves in mice: results of cold water tail flick tests*"), so that only one of these modules, of small size, can allow the therapeutic treatment of a patient or serve other applications such as stress reduction, generation of a feeling of well-being or the resolution of sleep disorders, without taking up space, and with reduced cost.

Advantageously, the waves have a power surface density value of between 5 and 35 mW/cm$^2$.

Thus, the waves transmitted comply with certain standards limiting their power towards human skin, but the power remains sufficient for an effect to be obtained, for example, a reduction in pain or a feeling of well-being.

Preferably, the waves have a frequency value between 3 and 120 gigahertz.

This is a particularly effective frequency band for the treatment of pain using millimeter waves.

Advantageously, it includes a rechargeable battery.

Therefore, it operates wirelessly. Alternatively, it may operate by wire, in order to deliver higher powers or over longer periods of time.

Preferably, the module is able to simultaneously expose at least 2.5 square centimeters of the surface to the waves. Thus, the module is capable of continuously exposing 2.5 cm$^2$ of a surface, in particular, skin, to the waves. Alternatively, the module may be capable of discontinuously exposing 2.5 cm$^2$ to waves, that is to say, several surface portions distributed over several different locations which, all together, represent 2.5 cm$^2$ of simultaneously irradiated surface.

For example, the module has several antennas transmitting waves simultaneously, the skin area of a patient covered by all of the antennas, and therefore by the module, representing at least 2.5 continuous square centimeters, irradiated in a homogeneous manner. This provides a continuous irradiated surface sufficient to induce the expected biological response. It should be noted that the frequency transmitted by the different antennas is not necessarily the same. The different antennas can transmit different frequencies, being supplied by different ASICs. Nevertheless, the frequencies remain within the band of interest.

Advantageously, the module comprises a heat sink comprising at least one of the following elements:
a flexible material;
a phase-change material;
a thermal buffer;
graphite; and
an elastomeric material.

Thus, the heat sink makes it possible to minimize the heating of the module, in particular if it is integrated into a device applied to the skin of a patient. This, again, makes it possible to comply with certain standards but also, more simply, to avoid excessive heating of the module or of the device in which it could be integrated.

Preferably, the surface being human or animal skin, the module comprises a skin detection unit capable of signaling the presence or absence of the skin to be exposed to the waves, and, preferably, capable of determining a distance separating the skin and the module.

Thus, the module transmits waves directly towards the subject's skin only if the skin is detected. If the skin is not detected, or if the distance is too great between the module and the skin, no transmission takes place. This way, sending waves in any direction is avoided and energy is saved. The power or other parameters of the waves transmitted may also be adapted according to the estimated distance between the module and the skin.

The invention further provides a portable device for transmitting electromagnetic waves, comprising a module described above.

Thus, the device can be easily worn by a human or animal patient and send waves in a predetermined manner or on command, for a therapeutic purpose, in order to generate a feeling of well-being or for any other purpose. The device is all the easier to be worn since the transmission module is small.

Preferably, the device is able to be worn at least in one of the following places:
around a wrist;
on a leg;
on an ankle;
on the back;
on an ear;
in the palm of a hand;
or more generally, any place presenting a highly innervated zone.

Thus, it is affixed at one of these sites, for example, in the manner of a watch around the wrist, so as to be worn by the patient without particular inconvenience.

An electromagnetic wave transmission method is also provided according to the invention, in which a module described above, worn by a human or animal subject, transmits electromagnetic waves having a power flux density of at least 0.5 milliwatts per square centimeter of skin towards the skin of the subject.

BRIEF DESCRIPTION OF THE DRAWINGS

Embodiments of the invention will now be presented by way of non-limiting examples and with reference to the drawings in which:

FIG. 1 illustrates the general framework of the invention. Patient 1 has chronic pain. He wears a device 10, according to a first embodiment and a first implementation of the invention, which treats the pain by transmitting electromagnetic millimeter waves to the skin of patient 1's wrist. In this case, this device 10 is in the general form of a wristwatch, and is affixed around the wrist in the same way as a watch. The device 10 comprises a control module 20 and a wave transmission module 22 illustrated schematically in FIG. 2 and in more detail in FIGS. 3, 5 and 6. The device 10 being in the general form of a watch, it may be a watch in which the modules 20 and 22 are integrated. Conversely, the functions of a watch may be integrated into device 10.

Figure 1:
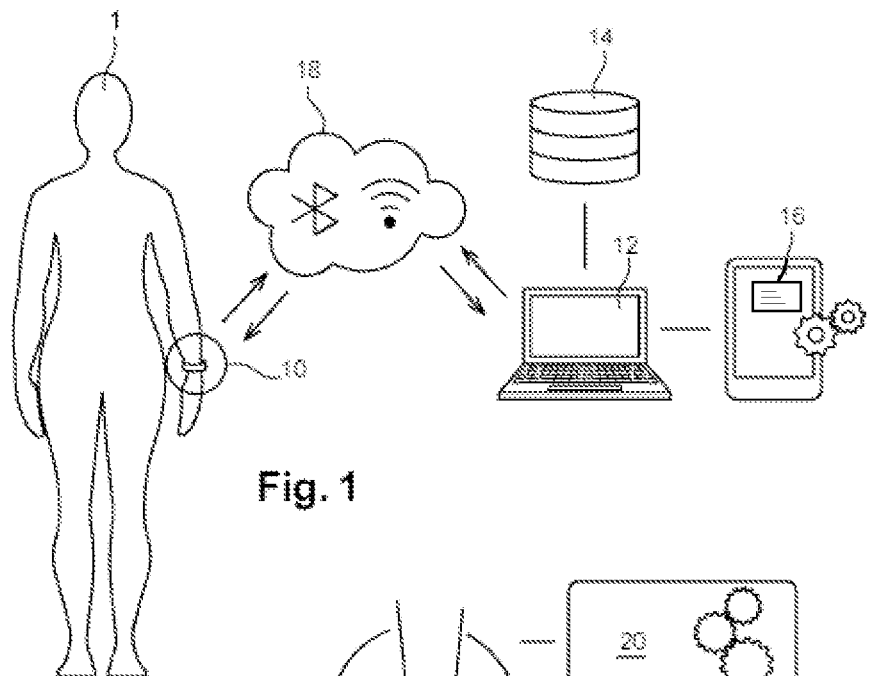
FIG. 1 is a block diagram of an embodiment of the invention.
Figure 2:
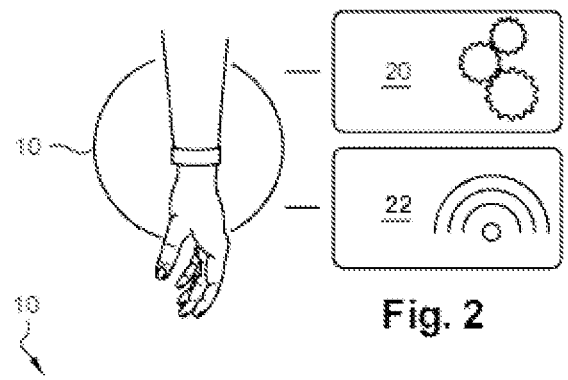
FIGS. 2 and 3, 5 and 6 are illustrations of a portable device according to a first embodiment of the invention.

The control module 20 controls the transmission module 22. The control module 20 is activated by the patient, but it may also be programmed by the patient or another user, on the device 10 directly with the button 23 or via a terminal such as the computer 12. The button 23 is provided with light-emitting diodes which can be activated to indicate an event to the patient, for example a lack of battery or the operation of a particular program in progress. The control module 20 is present in the upper part of the device 10 while the millimeter wave transmission module 22 is located in the lower part and therefore intended to be in contact with the skin of the lower part of the wrist.

The wave transmission module 22, integrated into the device 10, will now be described in detail. It is a transmission module according to a first embodiment. This type of module, as well as its other embodiments, may be integrated into any type of device aimed at transmitting waves, and not only into the device 10 in the form of a wristwatch. Its applications are not limited to the treatment of pain.

Figure 7:
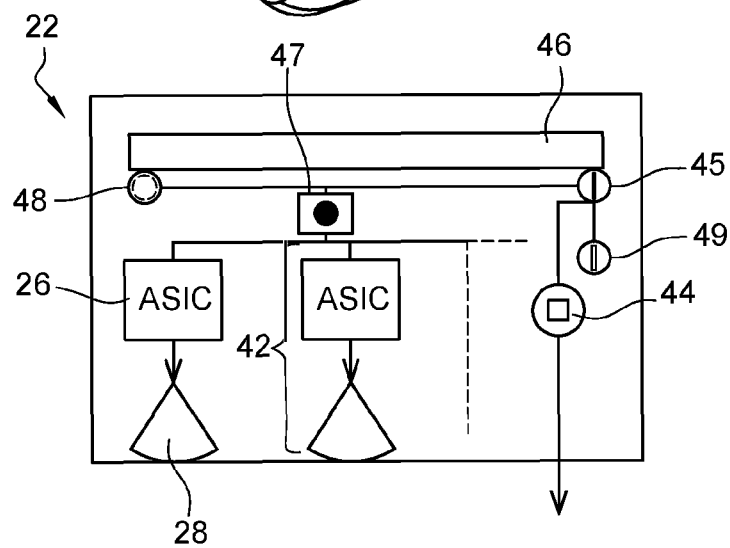
FIGS. 7 to 15 are diagrams of the components of a wave transmission module according to a first embodiment.

This transmission module 22, schematically illustrated in FIG. 7, presents several circuit-antenna pairs 42, a heat sink 46, a skin sensor 44, a power input 45, a digital control unit 47, a reference clock 48, and a temperature sensor 49.

Figure 8:
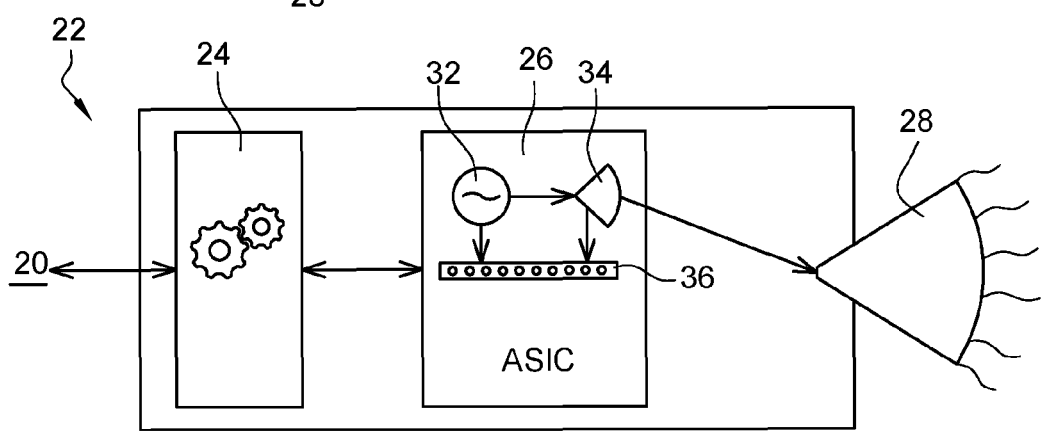
Figure 9:
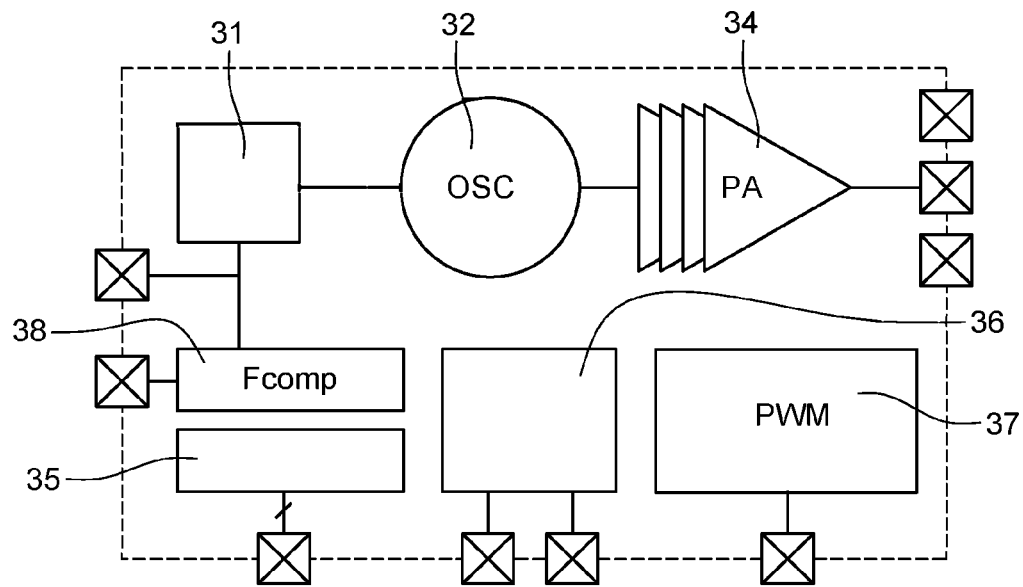
Figure 12:
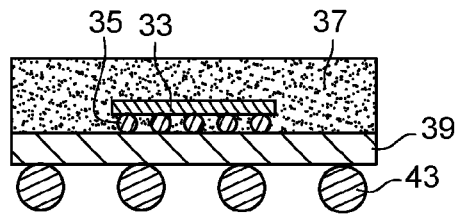
Figure 13:
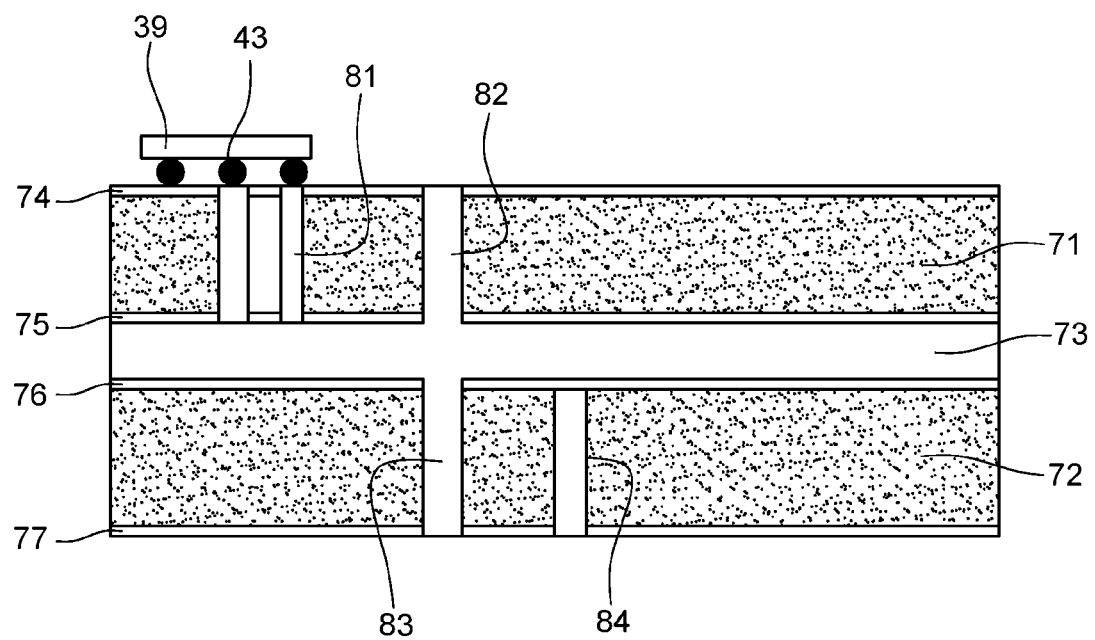

Each circuit-antenna pair 42, one of which being diagrammatically illustrated in FIG. 8, presents a control interface 24 in connection with the control module 20, an ASIC ("application-specific integrated circuit") 26 and an antenna 28. The interface 24 may be located within the control module 20. The ASIC 26, as illustrated in FIG. 8, comprises an oscillator 32, a power amplifier 34 and a digital part 36 for setting and controlling the component. Illustrated in more detail in FIG. 9, it also includes a frequency divider 31, a communication bus 35, a "pulse-width modulation" (PWM) control unit 37 and a frequency comparator 38. The oscillator 32 allows the ASIC operating frequency to be generated. The amplifier amplifies this signal so that the desired power is available at the component output. This power is adjustable between 0 and 20 mW. It may conceivably go up to 60 mW without any difficulty. The frequency comparator and the divider make it possible to check the operating frequency. The power management circuit makes it possible to supply all of the component's functions correctly. Finally, the "PWM" control unit makes it possible to transmit the HF output signal continuously or discontinuously. The framework of the ASIC is shown in FIG. 12. This ASIC 26 is manufactured using complementary metal-oxide semiconductor (CMOS) technology, which is known to the person skilled in the art and will not therefore be described in detail. More specifically, the transistors are of the "CMOS 65 nanometer" type. Alternatively, they could have been developed in silicon-germanium (SiGe) or even in gallium arsenide (GaAs). On the other hand, technologies of the "Gunn diode" type do not allow to achieve the desired minimum size and cost. Thus, the ASIC 26 includes a silicon integrated circuit 33 housed in a ball grid array (BGA)-type housing 37, a type of housing well known to the person skilled in the art, tailor-made for the ASIC 26, the housing also comprising balls (called "bumps") 35. As illustrated in FIG. 13, the circuit 33 is welded on two layers 71 and 72 of "HF" substrate 39 made of PTFE (Polytetrafluoroethylene) RO3003, for example, manufactured by Rogers, with an arrangement known as a "flip chip", which makes it possible to minimize the losses of electromagnetic radiation at high frequency. An alternative to RO3003 could be MT77 (for example, from Isola) impregnating woven glass fibers, or even RF301 (from Taconic), or any other material offering the same technical advantages as those mentioned. The two layers 71 and 72 are separated by a layer 73 of RO4450F as well as by copper layers 74, 75, 76 and 77. In addition, vias 81, 82, 83 and 84 make the connections between the different layers of the substrate. Understandably, the types of layers and their number could be different.

The frequency oscillator 32 is placed in a cavity (not shown) within the housing 37 which allows not to disturb the generated frequency. The size of this BGA housing 37 is, in this case, 2.2×2.2×0.9 millimeters. The connection to the antennas 28 is made by means of "balls" 43. This set of components makes it possible to minimize the losses of electromagnetic waves. It is the antenna 28 which transmits electromagnetic waves to the skin of the patient 1. Needless to say, the arrangement of the ASICs, control interface and antennas within the transmission module may be different.

Figure 14:
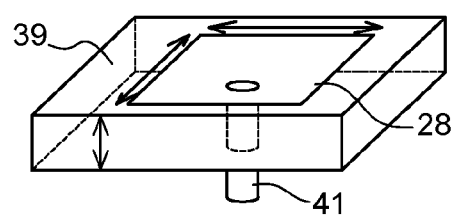

The terminal connection 41 between an ASIC 26 and its antenna 28 is visible in FIG. 14. Thus, a coaxial connection 41 ensures the transmission of the wave between the power amplifier 34 and the antenna 28. Antenna means generally any form of radiating element, provided that it is flat. This type of radiating element can be called a "patch".

Figure 15:
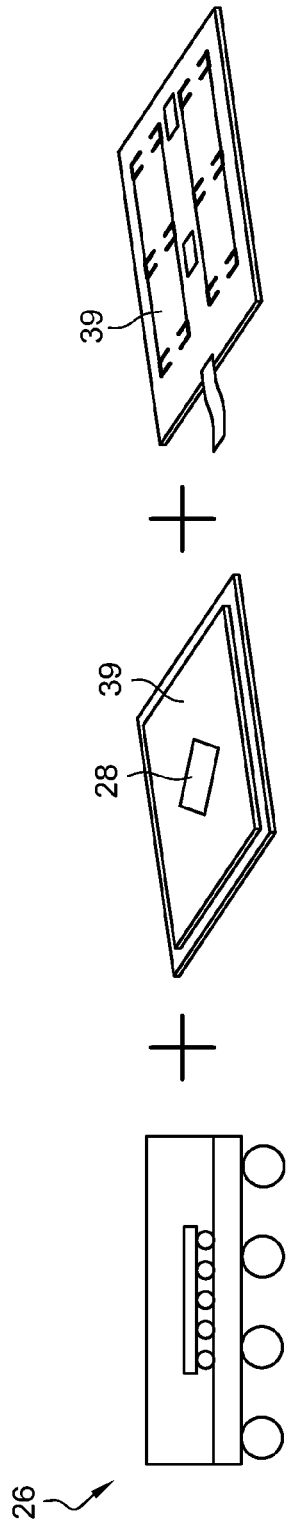

As shown in FIG. 15, the ASIC 26 and the antenna 28 are arranged on either side of the substrate 39.

Figure 10:
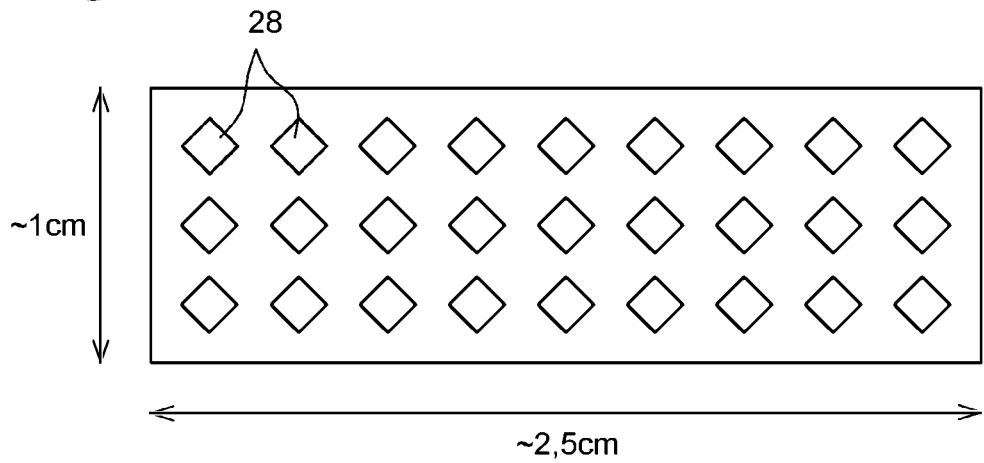
Figure 22:
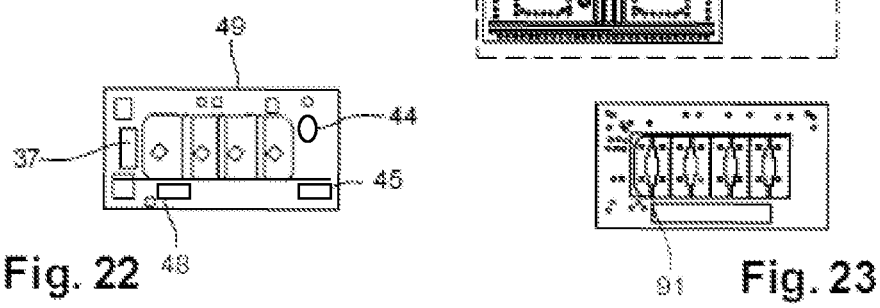

The set of antennas 28 forms an array of antennas, illustrated in FIG. 10. Rectangular-shaped here, this array of antennas, intended to be placed against the skin of patient 1 or at a short distance from it, is approximately 2.5 centimeters long by about 1 centimeter wide. It is provided, in this case, with 27 radiating elements 28 operating in near field, on the basis of three rows of nine antennas, aligned vertically and horizontally with respect to each other. These quantities and these arrangements are not limiting and others may be considered. The other elements of FIG. 7 and FIG. 9, in particular the temperature sensor 49, the skin sensor 44, the clock 48 and the power module 45 are arranged around this array of antennas, also called active area, as illustrated in FIG. 22 in a slightly different embodiment described below. The assembly formed by these elements and the active area located inside measures 37×20 mm and forms the transmission module 22, which may be integrated into a device such as a bracelet.

Figure 18:
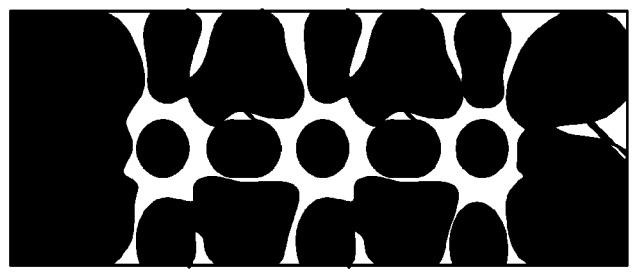
FIG. 18 is an illustration of a radiation of the module of FIGS. 14 and 15.
Figure 17:
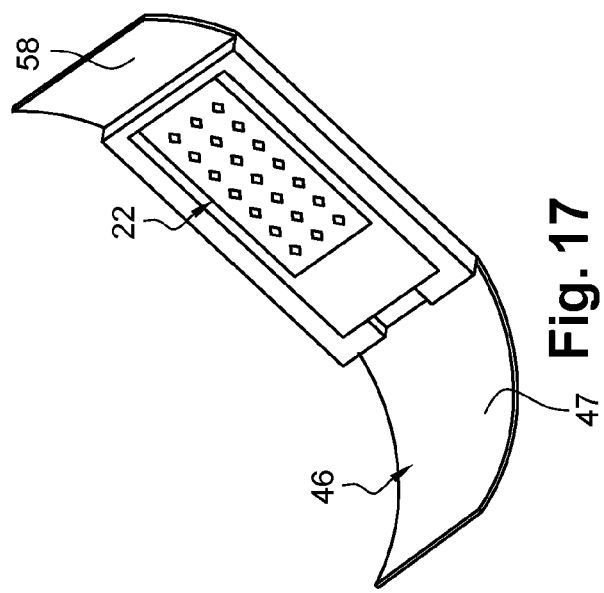
FIGS. 16 and 17 are illustrations of such a module respectively without and with heat sink.

This arrangement allows the active area to transmit waves homogeneously over 2.5 square centimeters of skin. "Homogeneous" means that the intensity of the waves arriving on the skin must not present a deviation greater than about 30% between its maximum value at one point and its minimum value at another. FIG. 18 shows the radiation emitted by the device on the patient's skin in a normal operating mode. The black forms correspond to radiation between 5 and 15 mW/cm², the white forms to radiation below 5 mW/cm². It is observed that 75% of the surface is irradiated by waves of density between 5 and 15 mW/cm². In general, the power density can be greater than 35 mW/cm², but the device is designed so that the power range used is of the order of 5 to 35 mW/cm² in normal operation, in particular for 30 minutes of continuous wave transmission. This operating mode is indeed the most usual, as will be described below.

Figure 11:
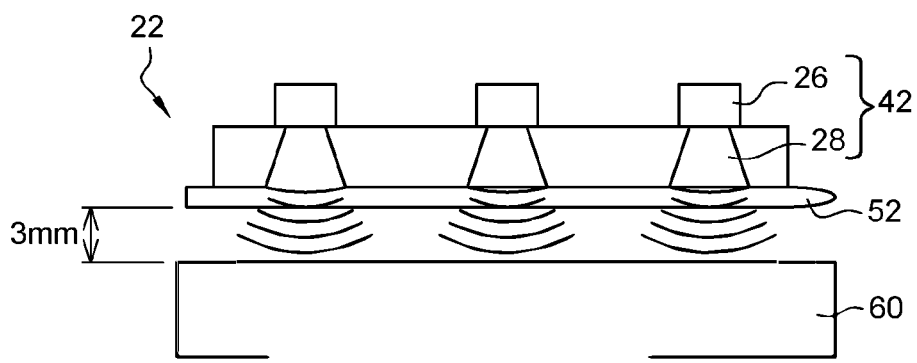

FIG. 11 illustrates an application of the module 22 for transmitting waves towards the skin 60 of patient 1. A distance of 3 millimeters separates the module from the skin of the patient in this case. Although the objective is to affix the device to the skin, it may happen that a slight space is created between the skin and the device. Furthermore, for more comfort and for reasons of biocompatibility, a silicone layer 52 separates the antennas from the skin, so that the skin does not have to directly support the antennas. Alternatively, it may be another material transparent to millimeter waves, such as polycarbonate. This layer 52 of silicone may measure from 1 to 2 millimeters, the design of the antennas allowing the layer 52 to have only little or no interference with the waves emitted.

Figure 16:
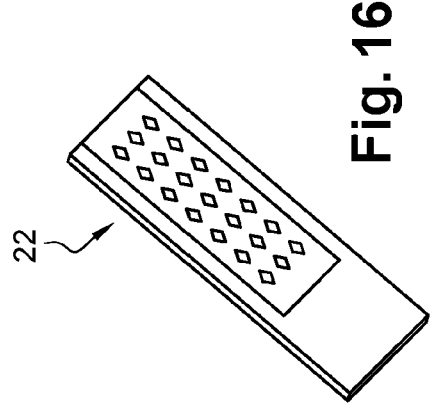

Overall, this wave transmission module 22, which can be called millimeter module (the waves being said to be "millimeter" in view of their frequency) or millimeter card, measures 37 millimeters in length, 20 millimeters in width and is 3 millimeters thick in this embodiment. Therefore, the volume of the millimeter module is 2.96 cubic centimeters. As shown in FIG. 16, it is therefore less than four, and even less than three cubic centimeters, which makes it possible to insert it into light low-volume devices, such as the device 10 in the form of a wristwatch. Having this volume and the described arrangement presenting 27 antennas, the ASICs 26 developed, coupled to the antennas 28, allow the millimeter module to transmit waves of frequency between 3 and 300 gigahertz, preferably between 30 and 120 gigahertz. The preferred frequency is 61.25 GHz+/−250 MHz. In all cases, the power flux density is at least 0.5 milliwatts per square centimeter, and the waves are transmitted simultaneously on a skin surface of 2.5 square centimeters. However, a millimeter wave treatment is effective at a power density starting from 0.5 milliwatts per square centimeter, preferably on a surface of at least 1 square centimeter. Therefore, the disclosed module makes it possible to carry out the treatment because it is easily integrated into any device due to its small volume.

It is understood that the ASICs, the antennas, as well as the whole of the millimeter module 22, may have different volumes, numbers and arrangements.

Figure 21:
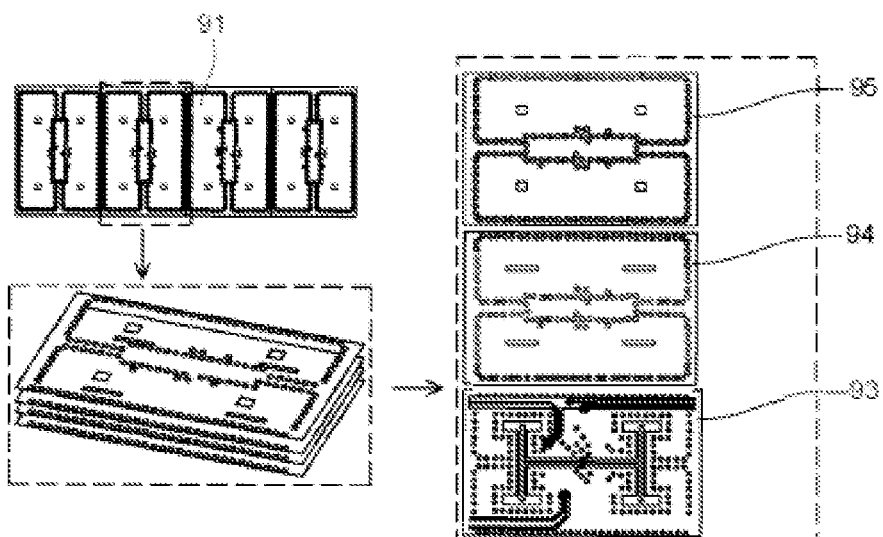
FIGS. 21 to 29 illustrate components of a module according to other embodiments of the invention.
Figure 23:
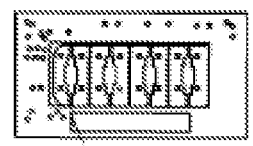
Figure 24:
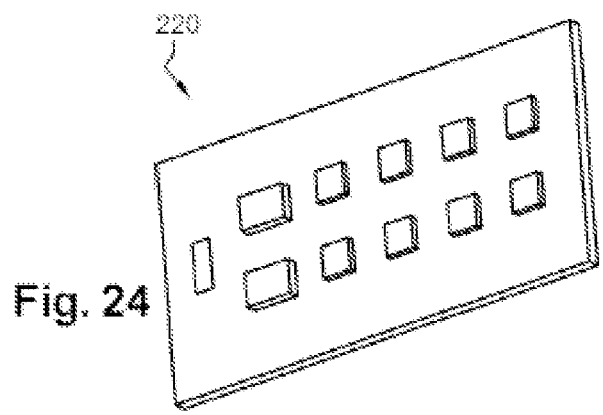
Figure 25:
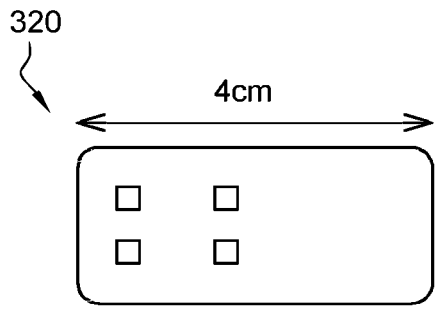
Figure 26:
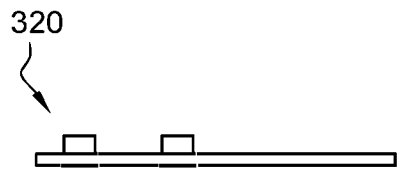
Figure 27:
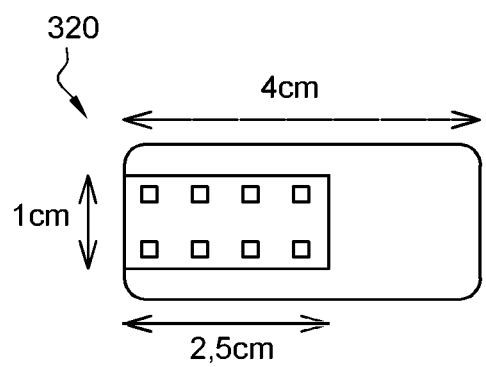
Figure 28:
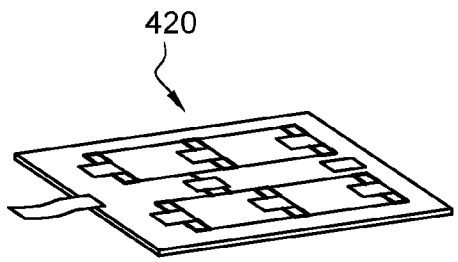
Figure 29:
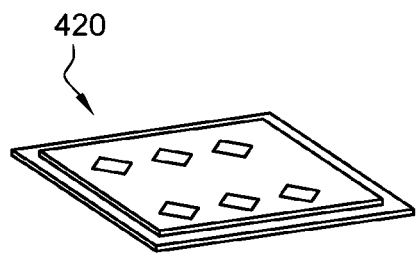

Thus, in a second embodiment, illustrated in FIGS. 21 to 23, the module's performances are identical. The difference is that an ASIC is coupled to four antennas on a surface of 10×6.25 mm Therefore, this ASIC/antenna pair covers a skin surface of 0.625 cm², on a PCB substrate 1 mm thick. Repeated four times side by side in the millimeter module illustrated in FIGS. 21 to 23, the four ASICs are each placed in a different "BGA" housing, whose size is 2.2 mm×2.2 mm×1 mm. The module, which then includes two rows of eight antennas and 4 ASICs (4 housings), thus makes it possible to continuously irradiate 2.5 cm² of skin surface.

An antenna array 91 according to this embodiment is illustrated in FIG. 21. Array 91, said to be a "resonant cavity" array, comprises four layers. The layer 92 allows the routing of digital and power signals. The second layer 93 represents the access lines to the antennas. The third layer 94 represents the coupling lines. Lastly, the fourth layer 95 is that from which the waves will be transmitted. This antenna array is also implemented in the previous embodiment, the only difference being the number of antennas and ASICs, and, therefore, the arrangement of these elements.

Alternatively, by placing the ASIC/four antenna pairs separately at different locations on the patient's skin, this 2.5 cm² surface is irradiated, but in several distinct areas. Likewise, each of these pairs may be used independently in order to ensure greater comfort or to be integrated into applications which require a smaller surface, or a lower power.

The skin sensor 44 of the embodiments described uses a capacitive type measurement making it possible to determine that the patient's skin is positioned near the millimeter module 22. Its structure is known to the person skilled in the art and is not limited to a capacitive measurement, any miniaturizable skin sensor being admissible. Connected to the control interface 24 and/or to the control module 20, the skin sensor 44 determines the presence or absence of human or animal skin. It is also able to determine the distance between the skin and the millimeter module. At 3 millimeters or less, wave transmission is allowed. Otherwise, the control module 20 can prevent the wave transmission. The objective here is to prevent inefficient wave transmission in order, on the one hand, to control the direction of the waves transmitted, and, on the other hand, to save energy. In the first embodiment, the skin sensor 44 is located outside the module, on a side of the device 10.

The millimeter module 22 may further comprise a rechargeable battery. Preferably, the device assembly comprising the module 22, such as the device 10, has a battery supplying both the control module 20 and the wave transmission module 22. This battery can be recharged conventionally from the mains or any other way. It is, naturally, interesting that its autonomy is several hours, even several days, so that the patient's portable device aimed at treating his pain is more convenient to use.

Some of the module components may needless to say, be placed outside thereof to better interact with the device comprising the module, such as the battery.

Apart from the control module 20, the millimeter module 22 and the skin sensor 44, the device 10 includes other components which will be described now.

Figure 3:
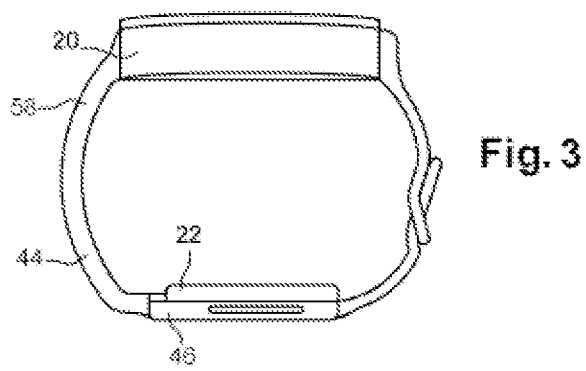

The band 58 of FIG. 3 is flexible and aims to adapt to the shape and size of the wrist, as would a conventional watch strap.

Figure 5:
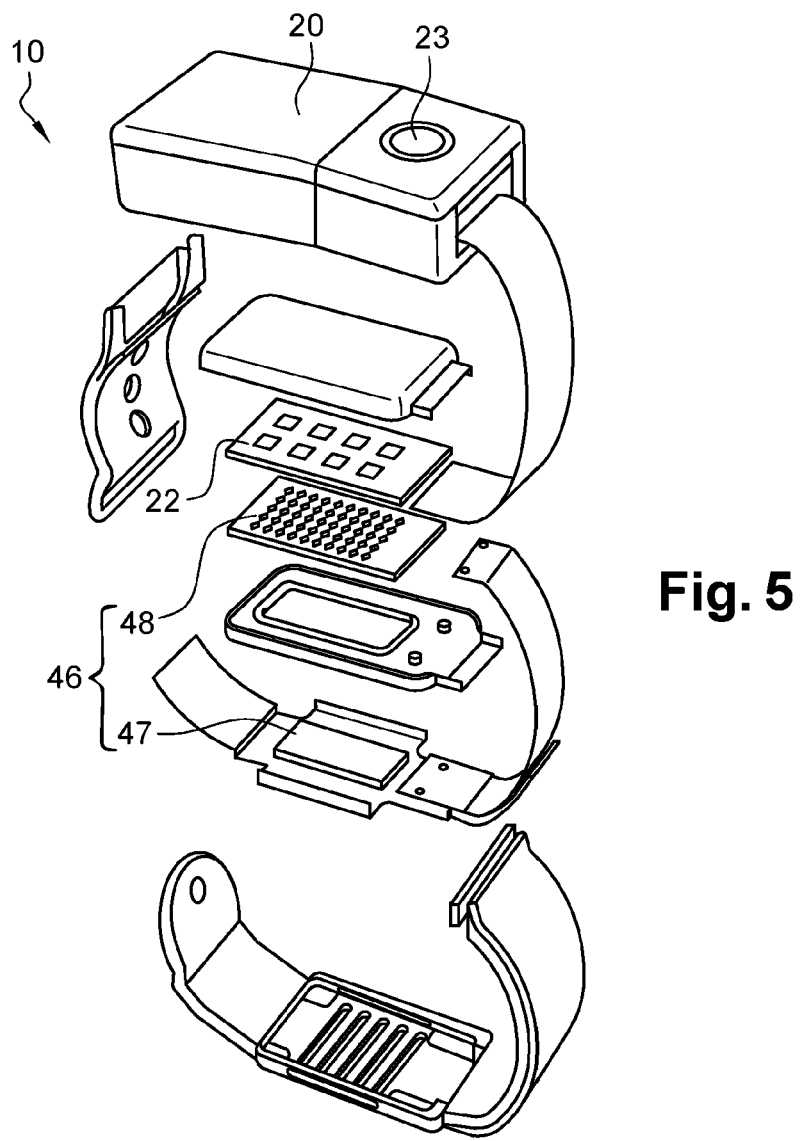
Figure 6:
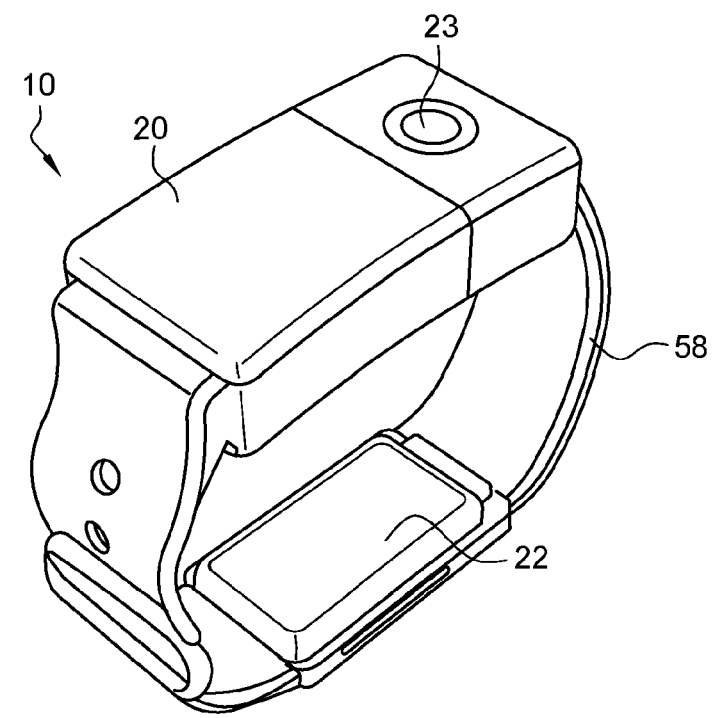

The device 10 also includes a dissipator 46, shown in FIG. 5, which may be considered as part of the millimeter module 22. In the present case, it is located outside this module, and comprises a flexible band 47 and a thermal buffer 48, the two components being inserted within the strap of the device 10. The band 47 is associated with graphite and rubber. The rubber allows the band to be flexible and therefore adaptable to the strap. The graphite is light and has good thermal conductivity. The band 47 may be made of another elastomeric material than rubber. It may also be made of a completely different material, which needs to be flexible in order to adapt to the shape of the device. The buffer 48 includes a phase-change material. Thus, during heat release due to the operation of the device, the phase-change material absorbs part of the calories generated and allows to maintain the overall temperature. The dissipator is arranged with the device in order to maintain the temperature of the surrounding area of the body below 43° C. for a continuous operation of the device of approximately 30 minutes. This temperature of 43° C. corresponds to maximum temperature standards set by certain authorities, and that is why the device is designed to comply with these standards. It could thus be designed differently if the maximum authorized temperature were higher. The temperature is monitored by the temperature sensor of the millimeter module 22.

The device 10 further includes a unit (not shown) for determining the impedance of the skin. This unit may be part of the millimeter module 22.

The frequency of the waves transmitted by the device 10 via the module 22 may be between 3 and 300 gigahertz for an effective treatment. However, the frequency of the device disclosed preferably varies between 30 and 120 gigahertz, with a preferred frequency around 60 gigahertz, in particular around 61.25 gigahertz.

Each component's dielectric properties, such as its permittivity, conductivity and loss tangent, had to be taken into account for the design of the module 22 and the device 10. Simulations and tests outside the nominal operating range of the 65 nm CMOS type ASIC transistors were carried out, and do not call into question the lifetime of the components with regard to the implementation of the millimeter wave treatment which will be disclosed below.

The implementation of pain treatment in the patient will now be disclosed.

This treatment aims to transmit waves towards an area of the patient's skin. The transmission generally lasts 30 minutes, at the rate of one transmission to two per day. The frequency, preferably between 30 and 120 gigahertz, is predetermined. It may possibly vary during a transmission, as does the power flux density which generally varies between 5 and 35 mW/cm$^2$, but can be lower or higher than this range. Needless to say, any other type of treatment is possible, in particular with longer and/or more frequent transmissions.

Figure 4:
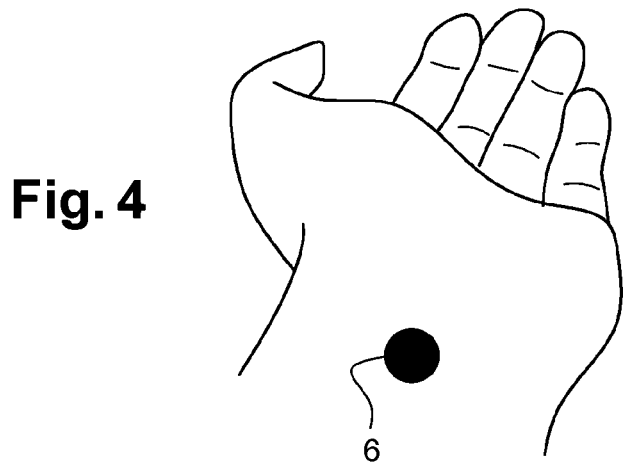
FIG. 4 illustrates a first embodiment of such a device.

In a first embodiment, the waves are transmitted by the module 22, integrated into the device 10 in the form of a wristwatch, towards the wrist, a highly innervated area, and may be placed on the acupuncture point Pericardium 6 referenced in FIG. 4, which is a known acupuncture point. It has indeed been shown that the transmission of waves to acupuncture points was particularly effective in the treatment of pain. In addition, very good results are also achieved for particularly innervated areas. Indeed, the stimulation of the nerve endings located under the skin induces a set of physiological actions called "systemic response", actions which in turn induce the synthesis of endogenous opioids (including the enkephalin) themselves responsible for decrease in pain. Thus, the more the wave transmission takes place in an area with a high density of nerve endings, the more the treatment is likely to be effective. Point Pericardium 6 is an acupuncture point at the same time located in an area rich in nerve endings. Therefore, a device transmitting waves towards this area is of utmost interest.

Furthermore, other potential benefits, described in the literature associated with this increase in the synthesis of opioids, are known, such as a decrease in heart rate and stress, improved sleep, or even a euphoric effect. Therefore, such benefits can be drawn from the device 10.

The frequency, the duration, and the power of the waves can be parameterized by means of the module 20 of the device 10. As illustrated in FIG. 1, it can be programmed in advance by means of a terminal, for example a computer 12, which can communicate with it by any telecommunication network, such as a Bluetooth or Wi-Fi type link 18. The computer 12 includes a database 14 on which is recorded a program 16 implementing the process or processes having a link with the invention, as well as various data allowing the implementation of the invention, in particular data entered by the patient 1 and data obtained by the device 10.

In addition, by determining the impedance of the skin using the impedance detection unit, the latter transfers to the control module 20 a characteristic data of the patient's skin. Parameters of the waves transmitted by the module 22 can then be modified automatically via the control unit 20, thanks to the program 16, or manually by the patient or another user. Thus, the device 10 adapts to the patient's skin. In other words, the electromagnetic field created is controlled by the characteristics of the skin. Il can also be modified based on the distance measured between the skin and the device, via the skin detector 44. The device may include other units determining and processing other data obtained directly from the patient, which can serve to adapt the parameters of the transmitted waves such as power, frequency and duration of transmission.

Other embodiments of the transmission module are illustrated in FIGS. 24 to 29. They differ from the previous embodiments by their number of ASICs and antennas. Thus, the module in FIG. 24 comprises 8 ASICs. In addition, one or more radiating elements may correspond to an ASIC. Thus, the module 320 comprises 4 ASICs for 8 radiating elements, at the rate of 2 radiating elements for 1 ASIC. Finally, module 420 comprises 6 ASICs and 6 radiating elements.

Figure 19:
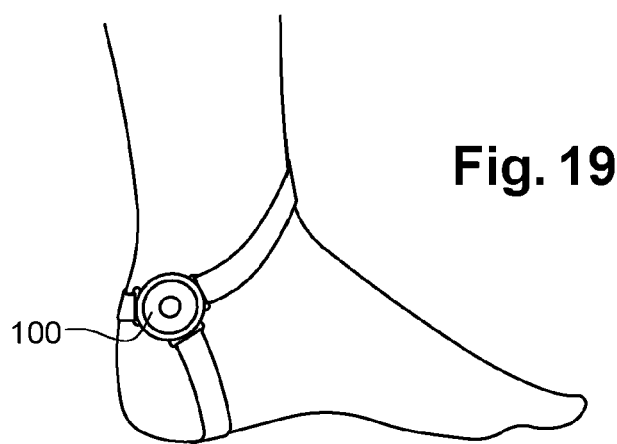
FIGS. 19 and 20 are illustrations of use according to the second and third embodiments of the invention.
Figure 20:
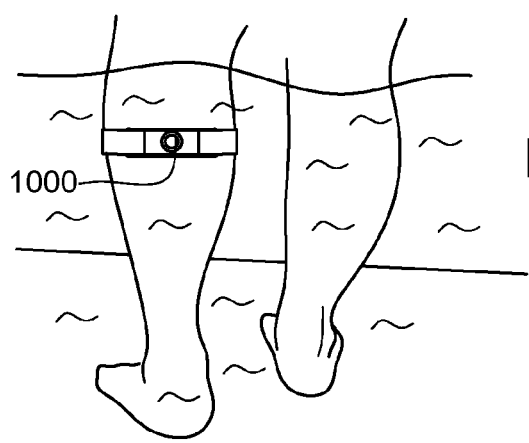

Furthermore, the transmission module may also be integrated into another device, for example intended to be worn by the patient in another part of the body. Thus, FIG. 19 illustrates a device 100 according to a second embodiment comprising the control and transmission modules placed on the ankle, while FIG. 20 illustrates such a device 1000 according to a third embodiment placed on the calf. Therefore, in these second and third embodiments, the waves are transmitted to other areas of the patient's body by means of devices which differ from the device 10 essentially to adapt to the targeted area of skin. In all cases, the miniaturization of the modules allows the device to be light and not bulky, so that it is easy to wear and not excessively burdensome.

Modifications are possible within this transmission module. For example, the structure of the antenna array may be different and present a "micro ribbon" type supply line or a coaxial probe. The antennas may be long slot antennas.

The control module may also be integrated into the electromagnetic transmission module.

Therefore, several embodiments and implementation modes were presented, which all allow the transmission of electromagnetic waves having a power surface density of at least 0.5 milliwatts per square centimeter of surface, a frequency value between 3 and 120 gigahertz, and simultaneously on a surface of at least 2.5 square centimeters, whether continuous or spread over several separate parts of the surface.

Aside from any pain treatment, the wave transmission module, possibly in conjunction with the control module, may be interesting for transmitting waves for other purposes, for example, to improve sleep, since it is particularly miniaturized, and therefore light. Consequently, it can be integrated into any device when it is necessary to send millimeter waves to a surface or in any direction.

Furthermore, the transmission module, or the control module, and/or the device integrating these modules, may be controlled remotely, from a terminal such as a computer, but also from a mobile terminal. For example, a mobile application comprising a pain treatment program may be saved on the mobile terminal, so that the patient programs his treatment himself, for example the power, the frequency, the duration and the time of wave transmission, or his doctor or any medical assistant programs these parameters remotely. In this case, the terminal comprises software presenting one or more interfaces allowing the user of the terminal to configure the device. The program allowing the implementation of the invention may be downloaded via a telecommunication network.

It may be added that the transmission module, as well as the device comprising it, may also be used in order to reduce the patient's stress or even bringing a feeling of well-being.

As a corollary, one can envisage the use of the transmission of electromagnetic waves within the framework of a program of improvement of a problem to be solved as perceived by the patient. The program may consist of the commitment on a series of supervised uses of the treatment with evolution of the exposure parameters (frequency, power, etc.). A discovery session, followed by a session adapted to the patient's feeling and the power of the effect perceived could be envisioned. The following sessions could also be adapted based on the measurement of said effect if sensors allow to measure it. Lastly, the treatment session could be triggered by the user through a program, or automatically if sensors allow to measure the need thereof.

Naturally, several modifications may be made to the invention without departing from the scope thereof.

The invention claimed is:

1. A portable device for transmitting electromagnetic waves, comprising:
   a control module;
   a transmission module comprising an application-specific integrated circuit housed in a ball grid array housing, the circuit including a frequency oscillator and a power amplifier, the transmission module having a volume less than 3 cubic centimeters,
   the transmission module controlled by the control module to, when placed at a surface, transmit waves having a power flux density between 5 and 35 milliwatts per square centimeter of the surface and a frequency value of between 61 and 61.5 gigahertz, and simultaneously expose the waves to at least 2.5 square centimeters of the surface, and
   the transmission module including a flexible heat sink configured to maintain the surface exposed to the waves at a temperature below 43° C., the flexible heat sink comprising a thermal buffer.

2. The device of claim 1, further comprising a capacitive skin sensor being able to signal a presence or absence of skin to be exposed to the waves, and determine a distance separating the skin and the device, using capacitive measurement.

3. The device of claim 1, suitable for being worn around a wrist, on one leg, on an ankle, on a back, on an ear, or in a palm of a hand.

4. The device of claim 1, further comprising a rechargeable battery.

5. The device of claim 1, wherein the flexible heat sink further comprises at least one of:
   a phase-change material;
   graphite; and
   an elastomeric material.

6. The device of claim 1, further comprising a unit for determining at least one data of the surface, wherein the at least one data of the surface includes an impedance data.

7. The device of claim 6, further comprising a processing unit configured to determine based on the determined data of the surface of at least one parameter of wave transmission.

8. The device of claim 1, further comprising a flexible band for securing the device around a wrist, a leg, or an ankle, wherein the control module and the transmission module are positioned on and attached to the flexible band.

9. The device of claim 8, wherein the control module is positioned on an opposite side of the flexible band from the transmission module.

10. The device of claim 9, wherein the control module includes a button for activation of the transmission module.

11. A method for transmitting electromagnetic waves, the method comprising steps of:
    transmitting the electromagnetic waves towards a skin of a human or animal subject with a transmitter worn by the human or animal subject, the electromagnetic waves having a power flux density of between 5 and 35 milliwatts per square centimeter of the skin and a frequency value between 61 and 61.5 gigahertz,
    wherein the transmitter includes an application-specific integrated circuit housed in a ball grid array housing, the circuit including a frequency oscillator and a power amplifier, and a flexible heat sink configured to maintain a surface of the skin at a temperature below 43° C., the flexible heat sink comprising a thermal buffer, and
    wherein the transmitter has a volume less than 3 cubic centimeters.

12. The method of claim 11, further comprising steps of:
    providing a unit detecting human or animal skin, and
    when the unit detects that the skin is located at three millimeters or less from the transmitter, the transmitter transmits the waves.

13. The method of claim 11, further comprising steps of:
    determining at least one impedance data of the skin; and
    depending on the at least one impedance data, adapting at least one parameter of the transmitter.

14. The method of claim 11, wherein the transmitting of the electromagnetic waves takes place at at least one predetermined acupuncture point of the human or animal subject.

15. The method of claim 11, wherein the transmitting of the electromagnetic waves is controlled by the transmitter.

16. The method of claim 15, wherein the transmitter is configured to be controlled by a terminal through a telecommunication network.

* * * * *